United States Patent [19]

Weissman et al.

[11] Patent Number: 5,087,570

[45] Date of Patent: Feb. 11, 1992

[54] HOMOGENEOUS MAMMALIAN HEMATOPOIETIC STEM CELL COMPOSITION

[76] Inventors: Irving L. Weissman, 662 Mirada Ave., Stanford, Calif. 94305; Gerald J. Spangrude, c/o Dr. Roland Scollay, The Walter & Eliza Hall Institute P.O. Royal Melbourne Hospital, VIC 3050, Australia; Christa Muller-Sieburg, 3672 Clairmont Dr., San Diego, Calif. 92117; Shelly Heimfeld, 700 Hermosa Way, Menlo Park, Calif. 94025

[21] Appl. No.: 192,378

[22] Filed: May 10, 1988

[51] Int. Cl.$^5$ .......................... A01N 1/02; C12N 5/02; C12P 21/00; A61K 39/00
[52] U.S. Cl. ..................................... 435/240.1; 435/2; 435/240.25; 424/85.91; 424/577; 436/808
[58] Field of Search ................... 435/240.25, 2, 240.1; 429/85.91; 436/808; 424/577

[56] References Cited

U.S. PATENT DOCUMENTS 4,714,680 12/1987 Civin ..................... 435/290.25

OTHER PUBLICATIONS

Whitlock and Witte, 1982. PNAS 79:3608–3612, Long-term Culture of B Lymphocytes & Their Precursors . . . .

Basch et al., Cell Separation Using Positive Imnunoselective Techniques J. Immun. Methods 56:200 1983.

Stites et al. Basic & Clinical Immun. 5th Ed. p. 765.

Muller-Sieburg et al. 1986, Cell 44:653–662, Isolation of Two Early B-Lymphocyte Progenitors . . . .

Primary Examiner—Elizabeth C. Weimar
Assistant Examiner—Suzanne Ziska

[57] ABSTRACT

Highly concentrated hematopoietic stem cell compositions are provided which are substantially free of differentiated or dedicated hematopoietic cells. The cells are obtained by subtraction of cells having particular markers and selection of cells having particular markers. The resulting composition may be used to provide for individual or groups of hematopoietic lineages, to reconstitute stem cells of the host, and to identify an assay for a wide variety of hematopoietic growth factors.

7 Claims, No Drawings

HOMOGENEOUS MAMMALIAN HEMATOPOIETIC STEM CELL COMPOSITION

INTRODUCTION

1. Technical Field

The field concerns methods for separating hematopoietic stem cells and the use of the resulting compositions for detecting growth factors and restoring blood cell lineages to a compromised host.

2. Background

All of mammalian blood cells are derived from a single progenitor stem cell. The stem cell is able to self-proliferate, so as to maintain a continuous source of regenerative cells. In addition, when subject to particular environments and/or factors, the stem cells may differentiate to dedicated progenitor cells, where the dedicated progenitor cells may serve as the ancestor cell to a limited number of blood cell types. These ancestor cells will go through a number of stages before ultimately achieving a mature cell.

The families of hematopoietic cells include lymphoid, myeloid, and erythroid cells. Each of these families plays an essential role in the wellbeing of the mammalian host. In many diseased states, the disease is a result of some defect in the maturation process. In other situations, such as transplantation, there is an interest in being able to prevent the hematopoietic system from rejecting the transplant. In this situation it may be desirable to inhibit rejection by irradiating the host so as to substantially inhibit the immune response to the congenic transplant.

In the case of neoplasia, the patient may be irradiated and/or treated with chemotherapeutic agents to destroy the neoplastic tissue. Since these and other treatments will kill rapidly proliferating cells, not only will the neoplastic cells be affected, but also the cells of the hematopoietic system. The host becomes immunocompromised and subject to opportunistic infection, as well as susceptible to bleeding due to loss of platelets.

Besides the situations indicated above, other situations may also be encountered, where there has been a severe insult to the immune system, resulting in a substantial reduction in stem cells. In these situations, it will frequently be desirable to restore stem cells to the host. However, the bone marrow from a congenic host will normally have a different histocompatibility profile from the immunocompromised host. In these situations, the bone marrow graft may recognize the host as foreign, resulting in graft versus host disease. However, this problem might not be encountered, where the only stem cells introduced are naive and may become adapted to the host, so as to be educated to recognize the host as native. There is, therefore, substantial interest in being able to obtain cells which are naive. In addition, these cells can be used in a variety of ways to identify growth factors, to screen growth factors, to be used in assays in studying the development of hematopoietic cells, and the like.

RELEVANT LITERATURE

Mouse thymic subsets may be divided by CD4 and CD8 markers. Swain, *Immunol. Rev.* (1983) 74:129; Fowlkes et al., *J. Exp. Med.* (1985) 162:802. Fowlkes et al. also report that double-negative thymocytes that repopulate the thymus in adoptive transfers express low levels of the Ly-1 antigen (Ly-$1^{lo}$). Monoclonal antibodies, provisionally designated stem cell antigens 1 and 2 (Sca-1 and Sca-2) have been reported. Aihara et al., *Eur. J. Immunol.* (1986) 16:1391. Limit dilution analysis for hematopoietic progenitors have been reported by Whitlock and Witte, *Proc. Natl. Acad. Sci. USA* (1982) 79:3608; and Whitlock et al., *Cell* (1987) 48:1009. Thy-1 is a surface marker of reconstituting bone marrow stem cells. Berman and Basch, *Exp. Hematol.* (1985) 13:1952, and Goldschneider et al., *J. Exp. Med.* (1978) 148:1351. Muller-Sieburg et al., *Cell* (1986) 44:653 describe Thy-$1^{lo}$Lin$^-$ cells. U.S. Pat. No. 4,714,680 describes a human stem cell composition.

SUMMARY OF THE INVENTION

Methods employing monoclonal antibodies are provided for the isolation of substantially homogeneous compositions of mammalian stem cells. The stem cells find use in regenerating the hematopoietic system of a host deficient in stem cells, in detecting and evaluating growth factors relevant to the development of hematopoietic cell lineages, and assaying for factors associated with hematopoietic cell development.

DESCRIPTION OF THE SPECIFIC EMBODIMENTS

Substantially homogeneous mammalian stem cell compositions are provided which may serve as the progenitors for all hematopoietic cell lineages. The stem cells are identified by specific markers which are identified with monoclonal antibodies. The substantially homogeneous composition may be obtained by selective isolation of cells free of markers associated with differentiated cells, while displaying epitopic characteristics associated with the stem cells.

The stem cells are characterized by both the presence of markers associated with specific epitopic sites identified by antibodies and the absence of certain markers. They may be further characterized by the level of a particular marker on the cell surface. It is not necessary that selection is achieved with a marker specific for stem cells. By using a combination of negative selection (removal of cells) and positive selection (isolation of cells), a substantially homogeneous stem cell composition can be achieved.

The isolation process will initially use a "relatively crude" separation to remove major cell families from the bone marrow or other hematopoietic cell source. For example, magnetic bead separations may be used initially to remove large numbers of cells, namely major cell populations of the hematopoietic system such as T-cells, various lineages, such as B-cells, both pre-B and B-cells, granulocytes, myelomonocytic cells, and platelets, or minor cell populations, such as megakaryocytes, mast cells, eosinophils and basophils. Generally, at least about 70%, usually 80% or more of the total hematopoietic cells will be removed. It is not essential to remove every dedicated cell class, particularly the minor population members, and the platelets and erythrocytes, at the initial stage. Since there will be positive selection at the end of the protocol, the dedicated cells will be left behind. However, it is preferable that there be positive selection for all of the cell lineages, so that in the final positive selection the number of dedicated cells present is minimized.

The stem cells may be characterized by having a stem cell antigen recognized by an antibody referred to as Sca-1, which monoclonal antibody is produced by the hybridoma E13 161-7 (*Blood,* 1986) 67:842), or 12-8, reported by Dr. Irving Bernstein, Fred Hutchinson Cancer Center, Seattle, WA. In addition, the cells are found to lack antigenic markers for various mature hematopoietic lineages, such as the surface markers, associated with pre-B and B-cells, identified by the monoclonal antibody to the B220 antigen RA3-6B2, the marker associated with granulocytes identified by the RB6 8C5 anti-Gr-1 antibody, the marker associated with myelomonocytic cells identified by the Mac-1 antibody, and the CD4 and CD8 markers associated with T-cells, or the species equivalents thereof. In addition, the cells contain significant but low levels of the cell surface differentiation antigen, the Thy-1 antigen in rodents and equivalent antigens in other mammalian cells, such as the human equivalent, the antibody to the human equivalent being reported by Dr. John Fabre, Radcliffe Hospital, Oxford, GB.

In order initially to obtain the subject stem cells, it is necessary to isolate the rare pluripotent stem cell from the other cells in bone marrow or other hematopoietic source. Initially, bone marrow cells may be obtained from a source of bone marrow, e.g. tibiae, femora, spine, fetal liver, and other bone cavities. Other sources of hematopoietic stem cells include fetal liver, fetal and adult spleen, yolk sac blood islands and the blood.

For isolation of bone marrow, an appropriate solution may be used to flush the bone, which solution will be a balanced salt solution, conveniently supplemented with fetal calf serum or other naturally occurring factors, in conjunction with an acceptable buffer at low concentration, generally from about 5 to 25 mM. Convenient buffers include Hepes, phosphate buffers, lactate buffers, etc.

Various techniques may be employed to separate the cells to initially remove cells of dedicated lineage. Monoclonal antibodies are particularly useful for identifying markers. The antibodies may be attached to a solid support to allow for separation. The separation techniques employed should maximize the retention of viability of the fraction to be collected. For "relatively crude" separations, that is, separations where up to 10%, usually not more than about 5%, preferably not more than about 1%, of the total cells present having the marker, may remain with the cell population to be retained, various techniques of differing efficacy may be employed. The particular technique employed will depend upon efficiency of separation, cytotoxicity of the methodology, ease and speed of performance, and necessity for sophisticated equipment and/or technical skill. Procedures for separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate. Techniques providing accurate separation include fluorescence activated cell sorters, which can have varying degrees of sophistication, e.g. a plurality of color channels, low angle and obtuse light scattering detecting channels, impedance channels, etc.

As exemplary of the subject method, in a first stage after incubating the cells from the bone marrow for a short period of time at reduced temperatures, generally $-10°$ to $10°$ C., with saturating levels of antibodies specific for T-cell determinants, the cells are washed with a fetal calf serum (FCS) cushion. The washed cells are then suspended in a buffer medium as described above and separated by means of the antibodies for the T-cell determinants.

Conveniently, the antibodies may be conjugated with markers, such as magnetic beads, which allow for direct separation, biotin, which can be removed with avidin bound to a support, fluorescers, e.g. fluorescein, which can use a fluorescence activated cell sorter, or the like, to allow for ease of separation of the T-cells from the other cells. Any technique may be employed which is not detrimental to the viability of the remaining cells.

Once the cells bound to the antibodies are removed, they may then be discarded. The remaining cells may then be incubated for a sufficient time at reduced temperature with a saturating level of antibodies specific for one or a mixture of cell differentiation antigens. The same or different mechanism for selecting for these cells as was used for removing the T-cells may be employed, where in the subject step, it is intended to use the unbound cells in subsequent stages.

The cells selected for as having the cell differentiation antigen are then treated successively or in a single stage with antibodies specific for the B-cell lineage, myelomonocytic lineage, the granulocytic lineage, the megakaryocytic lineage, platelets, erythrocytes, etc., although minor lineages may be retained, to be removed later. The cells binding to these antibodies are removed as described above, with residual cells desirably collected in a medium comprising fetal calf serum.

The residual cells are then treated with labeled antibodies selective but not specific for the stem cells, for mice the antibodies Sca-1 and Thy-1$^{lo}$, where the labels desirably provide for fluorescence activated cell separation (FACS). Multi-color analysis may be employed at this stage or previously. The cells are separated on the basis of an intermediate level of staining for the cell differentiation antigen, a high level of staining for Sca-1 and selected against dead cells and T-cells by providing for dyes associated with dead cells and T-cells as against stem cells. Desirably, the cells are collected in a medium comprising fetal calf serum. Other techniques for positive selection may be employed, which permit accurate separation, such as affinity columns, and the like. The method should permit the removal to a residual amount of less than about 1% of the non-stem cell populations.

The particular order of separation is not critical to this invention, but the order indicated is preferred. Preferably, cells will be initially separated by markers indicating unwanted cells, negative selection, followed by separations for markers or marker levels indicating the cells belong to the stem cell population, positive selection.

Compositions having greater than 90%, usually greater than about 95%, of stem cells may be achieved in this manner, where the desired stem cells are identified by having a low level of the Thy-1 cell differentiation antigen, being negative for the various lineage associated antigens and being positive for the Sca-1 antigen, which Sca-1 antigen is associated with clonogenic bone marrow precursors of thymocytes and progeny T-cells, or as already indicated, the mammalian, e.g. human counterparts thereof.

The stem cells appear as medium-size, lymphoid and round, intermediate in size between bone marrow lymphocytes and large myeloid cells. They are further distinguished by being late forming CFUs, which correlate with stem cells, whereby late forming is intended colonies of substantial size, at least about $2 \pm 0.8$ mm at day 12, while colonies at day 8, if any, are generally less than about 0.5±0.2 mm.

A pluripotent stem cell may be defined as follows: (1) gives rise to progeny in all defined hematolymphoid lineages; and (2) limiting numbers of cells are capable of fully reconstituting a lethally irradiated host from which the cells are obtained. In the subject compositions, fewer than 100 cells, usually fewer than 75 cells, more usually fewer than 50 cells, and as few as about 20 cells are able to fulfill the conditions indicated above. Thus, based on the standard set for the basic pluripotent stem cell, the subject compositions fulfill those requirements. Furthermore, the subject cells based on analysis of bone marrow cells appear to be in a range of from about 0.02 to 0.1% of bone marrow cells.

The subject method can be used to isolate stem cells from any vertebrate, particularly mammalian, species. Antibodies analogous to the antibodies employed for mice may be employed to obtain stem cells from primates, e.g. human, monkeys, gorillas, etc., domestic animals, bovine, equine, ovine, porcine, etc., or the like.

Once stem cells have been isolated, they may be propagated by growing in conditioned medium from stromal cells, such as those that can be obtained from bone marrow or liver associated with the secretion of factors, or in medium comprising cell surface factors supporting the proliferation of stem cells. Stromal cells may be freed of hematopoietic cells employing appropriate monoclonal antibodies for removal of the undesired cells, for example, with antibody-toxin conjugates, antibody and complement, etc.

The subject cell compositions may find use in a variety of ways. Since the cells are naive, they can be used to fully reconstitute a lethally irradiated host, desirably of the same species or genus, and can be used as a source of cells for specific lineages, by providing for their maturation, proliferation, and differentiation into one or more selected lineages by employing a variety of factors, such as erythropoietin, GM-CSF, G-CSF, M-CSF, interleukins, e.g. IL-1, -2, -3, -4, -5, -6, -7, etc., or the like, or stromal cells associated with the stem cells becoming committed to a particular lineage, or with their proliferation, maturation and differentiation.

The stem cells may also be used in the isolation and evaluation of factors associated with the differentiation and maturation of hematopoietic cells. Thus, the stem cells may be used in assays to determine the activity of media, such as conditioned media, evaluate fluids for cell growth activity, involvement with dedication to particular lineages, or the like.

The cells may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors or stromal cells associated with stem cell proliferation and differentiation.

The following examples are offered by way of illustration and not by way of limitation.

EXPERIMENTAL

Material and Methods

Mice

C57BL6/Ka (B/6, Thy-1.2) and C57BL6/KaThy-1.1 (B6-Thy1.1, Thy-1.1) were bred and maintained in the animal facility at Stanford University.

Antibodies

The rat monoclonal antibodies E13 161-7 (anti-stem cell antigen 1, Sca-1) and E3 81-2 (anti-stem cell antigen 2, Sca-2), as well as other putative anti-pre-T-cell antibodies (see Table I) have been previously described (Aihara et al., Eur. J. Immunol. (1986) 16.1391.)

Rat monoclonal antibodies RB6-8C5 (Anti-Gr-1, a granulocyte marker) and RA3-6B2 (anti-B220) provided by Dr. R. Coffman (DNAX Research Institute, Palo Alto, CA). Rat monoclonal antibodies 53-2.1 (anti-Thy-1.2), GK1.5 (anti-CD4), 53-6.72 (anti-CD8), 53-7.313 (anti-CD5), M1/70.15.11.5 (anti-Mac-1), and IM 7.8.1 (anti-phagocyte glycoprotein-1, Pgp-1, Ly-24) are all available through the American Type Culture

TABLE I

Tissue Distribution of Antigens Recognized by Putative Anti-Pre-T Cell Antibodies

| Antibody | | Percent of Bone Marrow Stained[1] | | Thymic Immuno-histochemistry |
|---|---|---|---|---|
| | | Total | Thy-1$^{lo}$ Fraction | |
| E13 | 161-7 (Sca-1) | 7.0 | 0.58 (33%) | Medulla, capsule, endothelium |
| E3 | 81-2 (Sca-2) | 12.2 | 0.54 (31%) | Cortex |
| E5 | 238-14-34 | 17.2 | 0.47 (27%) | Cortical clusters and medulla |
| E11 | 127-9 | 35.3 | 0.56 (32%) | Medulla |
| E3 | 238-2 | 47.2 | 0.98 (56%) | All thymocytes |
| E16 | 20-3 | 2.3 | 0.05 (3%) | Rare clusters |
| E16 | 33 | 1.0 | 0.07 (4%) | Cortex |

[1]Normal bone marrow was analyzed by two-color immunofluorescence for staining by the indicated monoclonal (Total) and for costaining with an anti-Thy-1 antibody (Thy-1$^{lo}$ fraction). The fraction of the total Thy-1$^{lo}$ cells stained is indicated in parentheses.

Collection. Mouse monoclonal antibody 19XE5 (anti-Thy-1.1) was provided by Dr. R. Nowinski (Genetic Systems Inc., Seattle WA).

Rat monoclonal antibodies were purified from tissue culture supernates by ammonium sulfate precipitation and ion exchange chromatography. Mouse monoclonal antibody 19XE5 was purified from tissue culture supernates by affinity chromatography on staphlococcal protein-A immobilized on dextran spheres. All monoclonal antibodies were derivatized with biotin-succinimide ester (Biosearch Research Chemicals, San Rafael, CA) or fluorescein isothiocyanate (Becton-Dickinson, Mountain View, CA) by standard methods. Mouse monoclonal 19XE5 was derivatized with allophycocyanin (APC) by Dr. P. Lalor (Walter and Eliza Hall Institute of Medical Research, Melbourne, Australia).

Goat anti-rat IgG, absorbed with mouse immunoglobulin, was obtained conjugated to Texas Red (TR) or fluorescein (FL) from Caltag Laboratories (South San Francisco, CA). Phycoerythrin (PE) conjugated to streptavidin and to goat-anti-rat Ig were obtained from Biomeda Corp. (Foster City, CA). FL-labeled avidin was obtained from Vector Laboratories, Inc. (Burlingame, CA) and TR-labeled avidin was purchased from Cooper Biomedical, Inc. (Westchester, PA).

Irradiation and reconstitution

Animals which were to be irradiated and reconstituted were maintained on antibiotics (neomycin 1.1 g/L; polymyxin 0.11 g/L ad libitum). Radiation (900 rads whole body) was delivered in two equal doses with a three-hour time interval, a method which allows some radiation repair in non-hematopoietic tissues (Geraci et al., J. Rad. Onc. Biol. Phys. (1977) 2:693) and thus enhances survival of reconstituted animals (Ferrara et al., *Transplantation* (1987) 43:461). A 250-kV x-ray machine (Phillips) was used to deliver 100 rads/min. All reconstitutions were by intravenous injection via the retroorbital plexus.

Cell suspension staining

All cell suspensions were prepared in Hank's Balanced Salt Solution (HBSS, Gibco Laboratories, Chagrin Falls, OH) supplemented with 5% calf serum (Sterile Systems Inc., Logan, UT), 10 mM HEPES buffer (Research Organics Inc., Cleveland, OH), and 5 mM sodium azide. Suspensions of bone marrow cells for reconstitution of irradiated animals were prepared in the same media, but containing 0.5 mM sodium azide. Cell suspension staining utilized directly labeled antibodies in most cases. When second stage anti-rat immunoglobulin stains were utilized in multicolor stains with other rat immunoglobulins, the cells were first incubated with the unlabeled antibody, followed by a wash and a labeled second stage antibody. After a second wash, the cells were resuspended in 10 μl of normal rat immunoglobulin (100 μg/ml, Pel-Freez Biologicals, Rogers, AK) and incubated for 10 minutes prior to addition of subsequent directly labeled reagents. All incubations and washes were performed on ice. Propidium iodide (PI) was added at 10 μg/ml during the last 5 minutes of staining for analysis, or at 2 μg/ml in the final cell suspension for sorting. PI was omitted from four-color immunofluorescence analyses.

Fluorescence activated cell sorter (FACS) analysis and sorting

A Becton-Dickinson FACS, modified as described (Parks and Herzenberg, *Meth. Enzymol* (1984) 108:197) was employed. The dual laser instrument allows 4 fluorescent parameters and 2 light scatter parameters to be recorded for each analyzed cell Residual erythrocytes and dead cells and debris were excluded from analysis by scatter gating and PI staining, or by scatter gating alone in 4-color analyses. Compensation for the special overlaps of FL and PE, FL and PI, and TR and APC was adjusted electronically as described (Parks and Herzenberg, 1984, supra). Four color stains were performed using several combinations of the same reagents conjugated to different fluorochromes, to assure that the results were consistent regardless of the various special overlaps of the fluorochromes. In addition, the results of 4-color analyses were corroborated by comparison with data from 2- and 3-color analyses.

For cell sorting, the stained samples were maintained at 4° C. throughout the sorting procedure. Sorted drops were collected in fetal calf serum (Sterile Systems, Inc., Logan, UT) in conical glass tubes in an ice bath. Three color sorts utilized PE to label hematolyphoid lineage-positive cells (e.g., cells expressing B220, Mac-1, Gr-1, CD4, and/or CD8), and PI to label dead cells, with both signals being detected and excluded in a single FACS channel. Following isolation of a cell population by FACS, the sample was diluted 1:1 in HBSS, centrifuged for 10 minutes at a RCF of 200, and resuspended in 50 or 100 μl of HBSS for hemocytometer counting.

Immunohistochemistry

Cryostat sections of lymphoid organs were prepared and stained as previously described (Reichert et al., *Cell* (1984) 38:89), using unmodified antibodies detected with biotinylated rabbit anti-rat immunoglobulin (absorbed with mouse serum) and horseradish peroxidase-Avidin D (both from Vector Laboratories, Burlingame, CA). The stain was visualized using 3-amino-9-ethylcarbazole (K and K Laboratories, Plainview, NY) as a substrate, the slides were counterstained lightly with hematoxylin, and permanent mounts were made using Crystal/Mount media (Biomeda Corp., Foster City, CA).

Purification of Pluripotent Hematopoietic Stem Cells

Bone marrow cells were obtained by flushing tibiae and femora of 10 C57BL/Ka-Thy-1.1 mice with Hanks Balanced Salt Solution without phenol red (Gibco Laboratories, Chagrin Falls, OH) supplemented with 5% fetal calf serum (FCS, Sterile Systems Inc., Logan, UT), and 10 mM Hepes buffer (Research Organics Inc., Cleveland, OH) (HBSS). The cells were incubated for 30 minutes on ice with saturating levels of directly fluoresceinated rat antibodies specific for the CD4 and CD8 T-cell determinants (antibodies GK-1.5 and 53-6.72, respectively. Following a wash with a FCS cushion, the cells were resuspended in 6 ml HBSS with 0.6 ml of magnetic beads coupled to sheep-anti-fluorescein antibodies (Advanced Magnetics Inc., Cambridge, MA), and incubated at room temperature for 20 minutes with constant mixing. The labeled T-cells were removed by magnetic separation (Bio-Mag Separator, Advanced Magnetics, Inc.) and discarded. The remaining cells were incubated for 30 minutes on ice with a saturating level of a directly fluoresceinated mouse antibody specific for the Thy-1.1 allelic determinant (antibody 19XE5) Magnetic beads were added and incubated as above, and the labeled cells were recovered by magnetic separation. Approximately 2.0% of the original cell suspension was recovered.

The magnetically-separated cells were incubated sequentially with the following reagents, each step being for 20 minutes on ice and being terminated with a wash in HBSS with a FCS cushion: anti-B220, -Mac-1, and -Gr01 in one incubation (rat antibodies RA3-6B2, M1/70.15.11.5, and RB6-8C5, respectively; these antibodies define the differentiated hematolymphoid lineages of B-cells, macrophages, and granulocytes); phycoerythrin-conjugated goat-anti-rat immunoglobulin (absorbed with mouse immunoglobulin, Biomeda Corp., Foster City, CA); normal rat immunoglobulin (Pel-Freez Biologicals, Rogers, AK); biotinylated rat-anti-Sca-1 (antibody E13 161-7); and Texas Red-conjugated avidin (Cooper Biomedical Inc., Westchester, PA). Following the final wash, the cells were resuspended in HBSS containing 2 μg/ml propidium iodide.

The labeled cells were analyzed and separated using a dual laser fluorescence activated cell sorter (FACS, Becton Dickinson, Mountain View, CA) modified as described previously. Cells to be sorted were selected on the basis of an intermediate level of fluorescein staining (Thy-1$^{lo}$), high right-angle scatter (due to the cell surface binding of magnetic beads), high levels of Texas Red (Sca-1+), intermediate forward scatter (to exclude RBC, free beads and cell aggregates), and low levels of phycoerythrin/propidium iodide (detected together in one FACS channel, which excludes dead cells and T-lineage cells). Sorted populations were greater than 90% pure with respect to their Thy-1$^{lo}$Lin−Sca-1+ phenotype, as assessed by reanalysis on the FACS. Cells were lysed by exposure to a lysing agent (American Scientific Products, McGraw Park, IL) and the nuclei were analyzed after staining with 10 μg/ml propidium iodide.

Spleen Colony Formation by Purified Stem Cells (Thy$^{lo}$Lin$^-$Sca$^+$)

Splenic colony-forming unit (CFU$_s$) activity was assessed 12 days after intravenous transfer of unseparated bone marrow cells or isolated hematopoietic stem cells into lethally irradiated (900r) syngeneic mice. By linear regression analysis, one splenic colony was formed per 10 hematopoietic stem cells transferred (r=0.91), or per 7200 unseparated bone marrow cells (r=0.93).

Thymic Colony Formation by Purified Stem Cells

Thymic colony-forming unit (CFU$_t$) activity was assessed 4 weeks after intrathymic transfer of isolated hematopoietic stem cells into sublethally irradiated (700r) mice, congenic to the stem cell population at the Thy-1 and Ly-5 loci. Thymic colonies, detected by FACS analysis of cells expressing donor allelic determinants, varied in size from $1 \times 10^5$ to $1 \times 10^8$ cells. Colony sizes did not vary with the number of cells injected, as some recipients of 3 cells contained thymic colonies which consisted of $10^7$ donor-derived cells. By limiting dilution analysis, one CFU$_t$ was transferred per 4 hematopoietic stem cells (r=0.9X).

Multiple Hematolymphoid Repopulation by Purified Stem Cells

Limiting numbers of hematopoietic stem cells will reconstitute multiple hematolymphoid lineages. Forty Thy-1$^{lo}$Lin$^-$Sca-1$^+$ cells (C57BL/6-Ly-5.2) were transferred intravenously into lethally-irradiated (900r) Ly-5 congenic mice (C57BL/Ka, Ly-5.1) along with 200 host-derived stem cells. At various times thereafter, donor-derived (Ly-5.2) cells were detected in the peripheral blood and phenotyped by 2-color FACS analysis. At 9 weeks post-reconstitution, 50% of the peripheral blood leukocytes in this mouse were derived from the 40 hematopoietic stem cells. These included 60% of the circulating T-cells, 50% of the B-cells, and 50% of the neutrophils.

Protection for Lethal Irradiation by Purified Stem Cells

Groups of 10-20 mice were lethally irradiated (900r) and reconstituted with graded numbers of purified hematopoietic stem cells intravenously. Fifty percent of the recipient animals survived the irradiation when 30 cells were transferred. In contrast, about 13,000 unseparated bone marrow cells were required to achieve the same level of radioprotection (Visser et al., *J. Exp. Med.* (1984) 59:1576).

Results

Identification of a Unique Subset of Medium-size Resting Thy-1$^{lo}$Lin$^-$ Bone Marrow Cells which Express the Sca-1 Antibody Bone marrow stem cells are restricted to a relatively rare subpopulation—the 0.1-0.2% of cells which are phenotyped as Thy-1$^{lo}$Lin$^-$(Muller-Sieburg et al., *Cell* (1986) 44:653-662). This population contains precursors for each hematolymphoid lineage, including thymocyte precursors. Another monoclonal antibody, now called Sca-1, also selects most, if not all clonogenic bone marrow precursors of thymocytes and their progeny T-cells (Aihara et al., 1986, supra). Only 20-30% of Thy-1$^{lo}$Lin$^-$ cells are Sca-1$^+$. Using a combination of immunomagnetic bead-aided removal of bone marrow T-cells, followed by immunomagnetic bead-aided enrichment of Thy-1$^{lo}$ cells, followed by FACS selection of Thy-1$^{lo}$Lin$^-$Sca-1$^+$ cells, a virtually pure population of medium-size lymphoid-appearing round cells were obtained. These cells are Thy-1$^{lo}$Lin$^-$Sca-1$^+$ as shown by FACS analysis. By forward scatter analysis they appear as a unimodal peak intermediate in size between bone marrow lymphocytes and large myeloid cells. Most, if not all of these cells are in the G$_0$/G$_1$ phase of the mitotic cycle; ≧97% have an amount of DNA by FACS analysis of propidium iodide stained nuclei.

The Thy-1$^{lo}$Lin$^-$Sca-1$^+$ Bone Marrow Cells Are a Virtually Pure Population of Primitive Myeloerythroid Stem Cells While the splenic colony-forming assay has been long regarded as an accurate reflection of pluripotent hematopoietic stem cell activity, recent evidence indicates that only the late-forming (day 12) CFUs correlate with true stem cell activity (Molineaux et al., *Exp. Hematol.* (1986) 14:710). As found by FACS analysis, Thy-1$^{lo}$Lin$^-$Sca-1$^+$ bone marrow cells contain a 1000-fold enrichment for day 12 CFUs when compared to whole bone marrow. There are essentially no day 8 CFUs in this fraction.

One splenic colony was observed per 10 intravenously-transferred stem cells. A seeding factor (f) for splenic engraftment complicates the question of the absolute number of stem cells that can form splenic colonies. If one accepts the splenic seeding factor as f=0.10-0.20 (Hendry, *Cell Tissue Kinet.* (1971) 4:211; Till and McCulloch, *Ser. Hemat.* (1972) Vol. V, 2:15), the actual frequency of cells in the Thy-1$^{lo}$Lin$^-$Sca-1$^+$ cell population capable of forming macroscopic 12 day splenic colonies is 1 in 1 to 2 cells.

The temporal evolution of splenic colonies can indicate the level of maturation of their progenitor cells, such that bone marrow cells that generate splenic colonies within 8 days are thought to be committed to a lineage of differentiation while cells that generate colonies only after 12 days have the characteristics of uncommitted, pluripotent progenitors. It would be expected that the candidate primitive myeloerythroid precursors give rise to 12-day spleen colonies, while the more differentiated precursors give rise predominantly to 8-day spleen colonies. Spleen colonies generated by the Sca-1$^+$ and Sca-1$^-$fractions of Thy-1$^{lo}$Lin$^-$bone marrow cells were investigated. The Sca-1$^+$ fraction gave rise to very few splenic colonies in an 8 day assay, and those colonies were quite small (0.48±0.06 mm). At day 12, however, the colonies generated by the Sca-1$^+$ fraction had a mean diameter of 2.12±0.69 mm. In contrast, colonies produced by the Sca-1$^-$fraction at 8 days and 12 days measured 1.10±0.24 mm and 2.32±0.82 mm, respectively. It is generally accepted that day 8 CFU$_s$ do not persist through day 12, so the colonies visualized in the Sca-1$^-$ fraction at day 8 and at day 12 may not be the products of the same progenitor cells. Thus, the Thy-1$^{lo}$Lin$^-$Sca-1$^-$ fraction of bone marrow may contain two distinct populations of cells.

The splenic colonies produced by both the Sca-1$^+$ and Sca-1$^-$fractions of Thy-1$^{lo}$Lin$^-$bone marrow cells were evaluated microscopically to determine whether either fraction was relatively enriched or depleted for erythroid or myeloid progenitors. The results indicated that the Sca-1⁻ fraction produced a distribution of colonies similar to that produced by whole bone marrow, and were enriched in pure erythroid colonies, especially at day 8. The Sca-1+ fraction, on the other hand, produced more myeloid and mixed colonies at day 9 and day 12.

TABLE II

Histological Analysis of Early and Late Spleen Colonies Derived from Thy-1$^{lo}$Lin⁻Sca-1⁻ and Thy-1$^{lo}$Lin⁻Sca-1+ Bone Marrow Cells

| Days Colonies Examined | Cell Source | Colony Morphology (%) | | | |
|---|---|---|---|---|---|
| | | Erythroid | Myeloid | Mixed | n |
| 8 | Thy-1$^{lo}$Lin⁻Sca-1+ | | 100 | | 3 |
| | Thy-1$^{lo}$Lin⁻Sca-1⁻ | 42 | 42 | 17 | 12 |
| 9 | Thy-1$^{lo}$Lin⁻Sca-1+ | 41 | 28 | 31 | 32 |
| | Thy-1$^{lo}$Lin⁻Sca-1⁻ | 80 | 5 | 15 | 20 |
| 12 | Thy-1$^{lo}$Lin⁻Sca-1+ | 27 | 27 | 46 | 15 |
| | Thy-1$^{lo}$Lin⁻Sca-1⁻ | 27 | 27 | 46 | 11 |

Groups of irradiated (900 rads) recipient mice received 1000 Thy-1$^{lo}$Lin⁻Sca-1⁻ cells or 200 Thy-1$^{lo}$Lin⁻Sca-1+ cells intravenously.

The Thy-1$^{lo}$Lin⁻Sca-1+ Bone Marrow Cells Are a Virtually Pure Population of Clonogenic Thymic Precursors The bone marrow contains a population of clonogenic, thymus-homing precursors (CFU$_t$) as revealed by their intravenous injection into lethally irradiated hosts. By limit dilution anlaysis these represent ~1/35000 bone marrow cells injected i.v., and ~1/5-8000 cells injected intrathymically. Colonies of thymocytes derived from the isolated Thy-1$^{lo}$Lin⁻Sca-1+ bone marrow cell fraction could be established following the intrathymic injection of as few as 5 cells. Intrathymic transfer of 10 or more of these cells resulted in thymic colonies in 95% or more of the injected thymic lobes. By limiting dilution analysis, the frequency of these cells with the ability to respond to the thymic microenvironment is approximately 1 in 4. This is likely to be an underestimate, as only ~30% of intrathymically injected bone marrow cells remain in the thymus a few hours after injection (Katsura, et. al., *J. Immunol.* (1986) 137:2434).

The Thy-1$^{lo}$Lin⁻Sca-1+ Bone Marrow Stem Cells Are a Virtually Pure Population of Multilineage Hematopoietic Stem Cells The definition of murine pluripotential hematopoietic stem cells is twofold: Each stem cell must be capable of giving rise to progeny in all defined hematolymphoid lineages; and limiting numbers of stem cells must be capable of fully reconstituting lethally irradiated mice, leading to their long-term survival. Limiting numbers of Thy-1$^{lo}$Lin⁻Sca-1+ bone marrow cells were able to repopulate T-cell, B-cell, and myeloid lineages when transferred into irradiated mice.

Forty Thy-1$^{lo}$Lin⁻Sca-1+ stem cells established multiple lineages of the hematolymphoid cells which can be identified by expression of the Ly-5.2 allelic determinant of the T-200 leukocyte common antigen. This antigen is expressed by all hematolymphoid lineages of cells with the exception of erythroblasts and erythrocytes (Scheid and Triglia, *Immunogenetics* (1979) 9:423). Approximately 50% of the peripheral blood leukocytes are derived from the 40 injected stem cells, with the remaining cells being derived from the 300 syngeneic Thy-1$^{lo}$Lin⁻ cells that were transferred along with the 40 congenic stem cells. Thus Thy-1$^{lo}$Lin⁻Sca-1+ cells are capable of multilineage reconstitution.

In a previous study it was demonstrated that 50% survival of lethally irradiated mice could be achieved with ~4×10⁴ bone marrow cells and ~100 Thy-1$^{lo}$Lin⁻ bone marrow cells (Whitlock et al., *Cell* (1987) 48:1009. In order to quantitate the activity of the Thy-1$^{lo}$Lin⁻Sca-1+ cells in this study, graded numbers of cells were intravenously transferred into lethally-irradiated syngeneic hosts. Incredibly, only 20-30 Thy-1$^{lo}$Lin⁻Sca-1+ bone marrow cells were required to rescue one-half of a group of lethally irradiated mice, where 4×10⁴ unfractionated bone marrow cells had the same result. As with the CFU$_s$ and CFU$_t$ assays, this represents a relative enrichment of 1000-fold over unseparated bone marrow. The Thy-1$^{lo}$Lin⁻Sca-1+ bone marrow subset represents only ~0.05% of all bone marrow cells. Thus the 50% reconstitution effected by ~4×10⁴ whole bone marrow cells is equivalent to ~20 Thy-1$^{lo}$Lin⁻Sca-1+ cells both numerically and in reconstitution of lethally irradiated mice. It appears unlikely that full long-term hematolymphoid reconstitution and survival of lethally irradiated hosts requires (or utilizes) any cells other than Thy-1$^{lo}$Lin⁻Sca-1+ cells; that is, most, if not all pluripotent mouse hematopoietic bone marrow stem cells are Thy-1$^{lo}$Lin⁻Sca-1+.

The above results demonstrate that a substantially homogeneous or homogeneous composition of pluripotent stem cells has been isolated. The cells tested showed the ability to reproduce all of the hematopoietic lineages and provide for a 50% survival rate in lethally irradiated hosts. The subject cells are shown to give rise to colonies when injected into thymus at a high efficiency and generate the T-cell population. The stem cells are therefore free of other cells which could interfere with identification of an assay for specific factors or which could provide for graft versus host disease upon injection into a host. The stem cells can be used to reconstitute immunologically active cells in an immunocompromised host, such as in the case of transplantations, retroviral infection, e.g. AIDS, or the like. Thus, the subject hematopoietic stem cells may be used in a wide variety of conditions where one or more hematopoietic lineages are deficient or the host is immunocompromised for any reason.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A cell composition consisting essentially of as the cellular population viable murine hematopoietic Sca-1+ stem cells from a genetically identical or congenic source.

2. A cell composition according to claim 1, wherein said cells are in a physiologically acceptable medium.

3. A method for preparing a cell composition according to claim 1, said method comprising:

(1) separating a bone marrow cell population into a population characterized by T-cell markers, high levels of the thy-1 differentiation marker and markers of major cell populations of dedicated hematopoietic cells and a substantially T-cell free, low level thy-1 population also substantially free of markers of major cell populations of dedicated hematopoietic cells by means of T-cell markers, thy-1 differentiation markers and dedicated hematopoietic cell markers to provide a substantially T-cell free, low level thy-1 differentiation marker population also lacking markers characteristic of major cell populations of dedicated hematopoietic cells for use in the next step, (2) separating said bone marrow cell population of (1) into cells that bind to the Sca-1 antibody and those that do not bind, wherein said cells which bind to the Sca-1 antibody are a substantially homogeneous population of stem cells.

4. A method according to claim 3, wherein the separation into a T-cell marker positive and T-cell marker negative population is performed with magnetic beads and step (2) is performed by fluorescence activated cell sorting.

5. A method according to claim 3, wherein said cell composition is a mouse cell composition and said antibody is the Sca-1 antibody.

6. A method for enhancing the level of at least one hematopoietic cell type in a murine host, said method comprising:
   administering to said host a congenic cell composition according to claim 1.

7. A method for augmenting the immune response of an immunocomprised murine host, said method comprising:
   administering to said host a congenic cell composition according to claim 1.

* * * * *